(12) United States Patent
Oh et al.

(10) Patent No.: US 7,709,627 B2
(45) Date of Patent: May 4, 2010

(54) OLIGONUCLEOTIDE PRIMER SET FOR AMPLIFYING TARGET SEQUENCE(S) OF NOROVIRUS, OLIGONUCLEOTIDE PROBE OR PROBE SET SPECIFICALLY HYBRIDIZING WITH TARGET SEQUENCE(S) OF NOROVIRUS, MICROARRAY IMMOBILIZED WITH THE PROBE OR PROBE SET, AND METHOD OF DETECTING NOROVIRUS USING THE PROBE OR PROBE SET

(75) Inventors: Ji-young Oh, Suwon-si (KR); Sook-young Kim, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 98 days.

(21) Appl. No.: 11/830,132

(22) Filed: Jul. 30, 2007

(65) Prior Publication Data

US 2008/0119369 A1    May 22, 2008

(30) Foreign Application Priority Data

Sep. 26, 2006 (KR) .................. 10-2006-0093717

(51) Int. Cl.
*C07H 21/04* (2006.01)
*C12Q 1/68* (2006.01)
*C12P 19/34* (2006.01)

(52) U.S. Cl. .................. 536/24.33; 536/24.3; 435/6; 435/91.1; 435/91.2

(58) Field of Classification Search .................. None
See application file for complete search history.

(56) References Cited

U.S. PATENT DOCUMENTS

| 5,445,934 | A | 8/1995 | Fodor et al. | |
| 5,744,305 | A | 4/1998 | Fodor et al. | |
| 2001/0053519 | A1 * | 12/2001 | Fodor et al. | 435/6 |
| 2005/0048475 | A1 | 3/2005 | Paul, III et al. | |
| 2005/0170338 | A1 | 8/2005 | Masuda et al. | |

FOREIGN PATENT DOCUMENTS

| KR | 1020060015669 A | 2/2006 |
| KR | 1020060041664 A | 5/2006 |

OTHER PUBLICATIONS

New England BioLabs® catalog, 1998, pp. 1-3.*
GenBank Accession No. AY587983, Sep. 14, 2004.
GenBank Accession No. AY587989, Sep. 16, 2004.
Korean Office Action dated Aug. 20, 2007 for Application No. 10-2006-0093717 (All references cited in Office Action are listed above).

* cited by examiner

*Primary Examiner*—Young J Kim
(74) *Attorney, Agent, or Firm*—Cantor Colburn LLP (57) ABSTRACT

Provided are an oligonucleotide primer set for amplifying at least one target sequence of the genomic RNA of norovirus, an oligonucleotide probe or probe set specifically hybridizing with at least one target sequence of the genomic RNA of norovirus, a microarray immobilized with the probe or probe set, and a method of detecting norovirus using the probe or probe set.

1 Claim, 3 Drawing Sheets

| G1-S01-pr1 | G1-S01-pr2 | G1-S01-pr2 | G1-S01-pr3 | G1-S01-pr3 | G1-S01-pr4 | G1-S01-pr4 | G1-S02-pr1 | G1-S02-pr1 | G1-S02-pr2 | G1-S02-pr2 |
| G1-S01-pr1 | G1-S01-pr2 | G1-S01-pr2 | G1-S01-pr3 | G1-S01-pr3 | G1-S01-pr4 | G1-S01-pr4 | G1-S02-pr1 | G1-S02-pr1 | G1-S02-pr2 | G1-S02-pr2 |
| G1-S02-pr3 | G1-S02-pr4 | G1-S02-pr4 | G1-S03-pr1 | G1-S03-pr1 | G1-S03-pr2 | G1-S03-pr2 | G1-S03-pr3 | G1-S03-pr3 | G2-S01-pr1 | G2-S01-pr1 |
| G1-S02-pr3 | G1-S02-pr4 | G1-S02-pr4 | G1-S03-pr1 | G1-S03-pr1 | G1-S03-pr2 | G1-S03-pr2 | G1-S03-pr3 | G1-S03-pr3 | G2-S01-pr1 | G2-S01-pr1 |
| G2-S01-pr2 | G2-S01-pr3 | G2-S01-pr3 | | | | | | | | |
| G2-S01-pr2 | G2-S01-pr3 | G2-S01-pr3 | | | | | | | | |

FIG. 3

SEQUENCE LISTING

<160> NUMBER OF SEQ ID NOS: 11

<210> SEQ ID NO 1
<211> LENGTH: 22
<212> TYPE: DNA
<213> ORGANISM: Artificial Sequence
<220> FEATURE:
<223> OTHER INFORMATION: forward primer for G1-S02

<400> SEQUENCE: 1
gacccagctg gttggtttgg aa                                            22

<210> SEQ ID NO 2
<211> LENGTH: 22
<212> TYPE: DNA
<213> ORGANISM: Artificial Sequence
<220> FEATURE:
<223> OTHER INFORMATION: reverse primer for G1-S02

<400> SEQUENCE: 2
gcgtcattcg acgccatctt ca                                            22

<210> SEQ ID NO 3
<211> LENGTH: 24
<212> TYPE: DNA
<213> ORGANISM: Artificial Sequence
<220> FEATURE:
<223> OTHER INFORMATION: forward primer for G2-S01

<400> SEQUENCE: 3
agatgctcca agcacaaatt gagg                                          24

<210> SEQ ID NO 4
<211> LENGTH: 22
<212> TYPE: DNA
<213> ORGANISM: Artificial Sequence
<220> FEATURE:
<223> OTHER INFORMATION: reverse primer for G2-S01

<400> SEQUENCE: 4
gcatcaggag cccagtacct tg                                            22

```
<210> SEQ ID NO 5
<211> LENGTH: 25
<212> TYPE: DNA
<213> ORGANISM: Artificial Sequence
<220> FEATURE:
<223> OTHER INFORMATION: probe specific for G1-S02

<400> SEQUENCE: 5
ccactaaaaa gttgcaacag ggtat                                              25

<210> SEQ ID NO 6
<211> LENGTH: 22
<212> TYPE: DNA
<213> ORGANISM: Artificial Sequence
<220> FEATURE:
<223> OTHER INFORMATION: probe specific for G1-S02

<400> SEQUENCE: 6
ggaagttaaa cgggcaatgc tc                                                 22

<210> SEQ ID NO 7
<211> LENGTH: 24
<212> TYPE: DNA
<213> ORGANISM: Artificial Sequence
<220> FEATURE:
<223> OTHER INFORMATION: probe specific for G1-S02

<400> SEQUENCE: 7
tgctcctaga gggtggattc tctg                                               24

<210> SEQ ID NO 8
<211> LENGTH: 22
<212> TYPE: DNA
<213> ORGANISM: Artificial Sequence
<220> FEATURE:
<223> OTHER INFORMATION: probe specific for G1-S02

<400> SEQUENCE: 8
atcaacgccc ccatgacaaa gg                                                 22

<210> SEQ ID NO 9
<211> LENGTH: 24
<212> TYPE: DNA
<213> ORGANISM: Artificial Sequence
<220> FEATURE:
<223> OTHER INFORMATION: probe specific for G2-S01

<400> SEQUENCE: 9
aaggtggcat ggatttttac gtgc                                               24

<210> SEQ ID NO 10
<211> LENGTH: 22
<212> TYPE: DNA
<213> ORGANISM: Artificial Sequence
<220> FEATURE:
<223> OTHER INFORMATION: probe specific for G2-S01

<400> SEQUENCE: 10
ggcatggatt tttacgtgcc ca                                                 22

<210> SEQ ID NO 11
<211> LENGTH: 22
<212> TYPE: DNA
<213> ORGANISM: Artificial Sequence
<220> FEATURE:
<223> OTHER INFORMATION: probe specific for G2-S01
```

```
<400> SEQUENCE: 11
gatcgcaatc tggctcccag tt                                              22
```

OLIGONUCLEOTIDE PRIMER SET FOR AMPLIFYING TARGET SEQUENCE(S) OF NOROVIRUS, OLIGONUCLEOTIDE PROBE OR PROBE SET SPECIFICALLY HYBRIDIZING WITH TARGET SEQUENCE(S) OF NOROVIRUS, MICROARRAY IMMOBILIZED WITH THE PROBE OR PROBE SET, AND METHOD OF DETECTING NOROVIRUS USING THE PROBE OR PROBE SET

CROSS-REFERENCE TO RELATED PATENT APPLICATION

This application claims priority from Korean Patent Application No. 10-2006-0093717, filed on Sep. 26, 2006, in the Korean Intellectual Property Office, the disclosure of which is incorporated herein in its entirety by reference.

BACKGROUND OF THE INVENTION

1. Field of the Invention

The present invention relates to an oligonucleotide primer set for amplifying at least one target sequence of genomic RNA of norovirus, an oligonucleotide probe or probe set specifically hybridizing with at least one target sequence of the genomic RNA of norovirus, a microarray immobilized with the probe or probe set, and a method of detecting norovirus using the probe or probe set.

2. Description of the Related Art

Noroviruses are commonly known as causative viruses of viral food poisoning. Noroviruses are members of the human Caliciviridae family, and contain single-stranded RNA genomes with the sequence of about 7,000 nucleotides. Noroviruses are also called Small Round Structured Viruses (SRSVs).

It is estimated that about 20% of food poisoning cases is caused by viruses. Noroviruses are detected in about 80% of viral food poisoning cases. The main infection source is food, and norovirus infection associated with raw oyster consumption frequently becomes an issue. Noroviruses have also been detected in (sporadic) acute gastroenteritis among infants, and the possibility of person-to-person transmission of noroviruses has been suggested. Thus, testing for noroviruses is an important issue in terms of public health and food quality control. Therefore, it is necessary to develop a highly sensitive and rapid testing method capable of detecting all or most subtypes using a gene amplification process.

U.S. Patent Laid-Open Publication No. 2005/0170338 discloses a probe capable of binding with the genomic RNA of norovirus, and a primer capable of amplifying a specific sequence of the genomic RNA of norovirus. U.S. Patent Laid-Open Publication No. 2005/0048475 discloses a primer capable of amplifying a specific sequence of the genomic RNA of norovirus to detect norovirus.

In spite of the above-described conventional techniques, no primer set capable of amplifying at least one target sequence selected from an intergenic region between ORF1 and ORF2 (capsid coding region) and an intergenic region between ORF2 and ORF3 in norovirus is disclosed. No probe specific to the at least one target sequence is also disclosed.

SUMMARY OF THE INVENTION

The present invention provides a primer set capable of amplifying a target sequence of norovirus.

The present invention also provides a probe or probe set for detecting norovirus, which is specific to a target sequence amplified using the primer set.

The present invention also provides a microarray immobilized with the probe or probe set.

The present invention also provides a method of detecting norovirus using the probe or probe set.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention provides an oligonucleotide primer set for amplifying at least one target sequence of the genomic RNA of norovirus, the oligonucleotide primer set including at least one oligonucleotide set selected from the group consisting of: an oligonucleotide set including at least one oligonucleotide selected from the group consisting of oligonucleotides which include a fragment of at least 10 contiguous nucleotides present in a nucleotide sequence as set forth in SEQ ID NO: 1 and at least one oligonucleotide selected from the group consisting of oligonucleotides which include a fragment of at least 10 contiguous nucleotides present in a nucleotide sequence as set forth in SEQ ID NO: 2; and an oligonucleotide set including at least one oligonucleotide selected from the group consisting of oligonucleotides which include a fragment of at least 10 contiguous nucleotides present in a nucleotide sequence as set forth in SEQ ID NO: 3 and at least one oligonucleotide selected from the group consisting of oligonucleotides which include a fragment of at least 10 contiguous nucleotides present in a nucleotide sequence as set forth in SEQ ID NO: 4.

In the primer set of the present invention, the target sequence may be at least one selected from an intergenic region between ORF1 and ORF2 (capsid coding region) and an intergenic region between ORF2 and ORF3 in norovirus. Noroviruses are divided into two groups: Norwalk-like viruses and Sapporo-like viruses. Generally, the genomic RNA of norovirus is composed of three open reading frames (ORFs): ORF1, ORF2, and ORF3. The target sequence of the present invention is selected from overlapping regions of the three ORFs, i.e., the ORF1-ORF2 intergenic region and the ORF2-ORF3 intergenic region.

The primer set of the present invention may be an oligonucleotide primer set for amplifying an intergenic region between ORF1 and ORF2 in norovirus, which includes an oligonucleotide set including at least one oligonucleotide selected from the group consisting of oligonucleotides which include a fragment of at least 10 contiguous nucleotides present in the nucleotide sequence as set forth in SEQ ID NO: 1 and at least one oligonucleotide selected from the group consisting of oligonucleotides which include a fragment of at least 10 contiguous nucleotides present in the nucleotide sequence as set forth in SEQ ID NO: 2.

The primer set of the present invention may be an oligonucleotide primer set for amplifying an intergenic region between ORF2 and ORF3 in norovirus, which includes an oligonucleotide set including at least one oligonucleotide selected from the group consisting of oligonucleotides which include a fragment of at least 10 contiguous nucleotides present in the nucleotide sequence as set forth in SEQ ID NO: 3 and at least one oligonucleotide selected from the group consisting of oligonucleotides which include a fragment of at least 10 contiguous nucleotides present in the nucleotide sequence as set forth in SEQ ID NO: 4.

The primer set of the present invention may be an oligonucleotide primer set for amplifying an intergenic region between ORF1 and ORF2 and an intergenic region between ORF2 and ORF3 in norovirus, which includes an oligonucleotide set including an oligonucleotide having the nucleotide sequence as set forth in SEQ ID NO: 1 and an oligonucleotide having the nucleotide sequence as set forth in SEQ ID NO: 2 and an oligonucleotide set including an oligonucleotide having the nucleotide sequence as set forth in SEQ ID NO: 3 and an oligonucleotide having the nucleotide sequence as set forth in SEQ ID NO: 4.

As used herein, the term "primer" refers to a single-stranded oligonucleotide sequence complementary to a nucleic acid sequence sought to be copied and serves as a starting point for synthesis of a primer extension product. The length and sequence of a primer are determined to be suitable for initiating the synthesis of an extension product. Preferably, a primer is about 5-50 nucleotides in length. The length and sequence of a primer can be appropriately determined according to the complexity of a target DNA or RNA and the use conditions of a primer, e.g., a temperature, and an ionic strength.

Taking into consideration that the genome sequences of noroviruses have high diversity, the primer set of the present invention was designed from highly conserved regions of 100 isolates of noroviruses, i.e., the ORF1-ORF2 intergenic region and the ORF2-ORF3 intergenic region.

Figure 1:
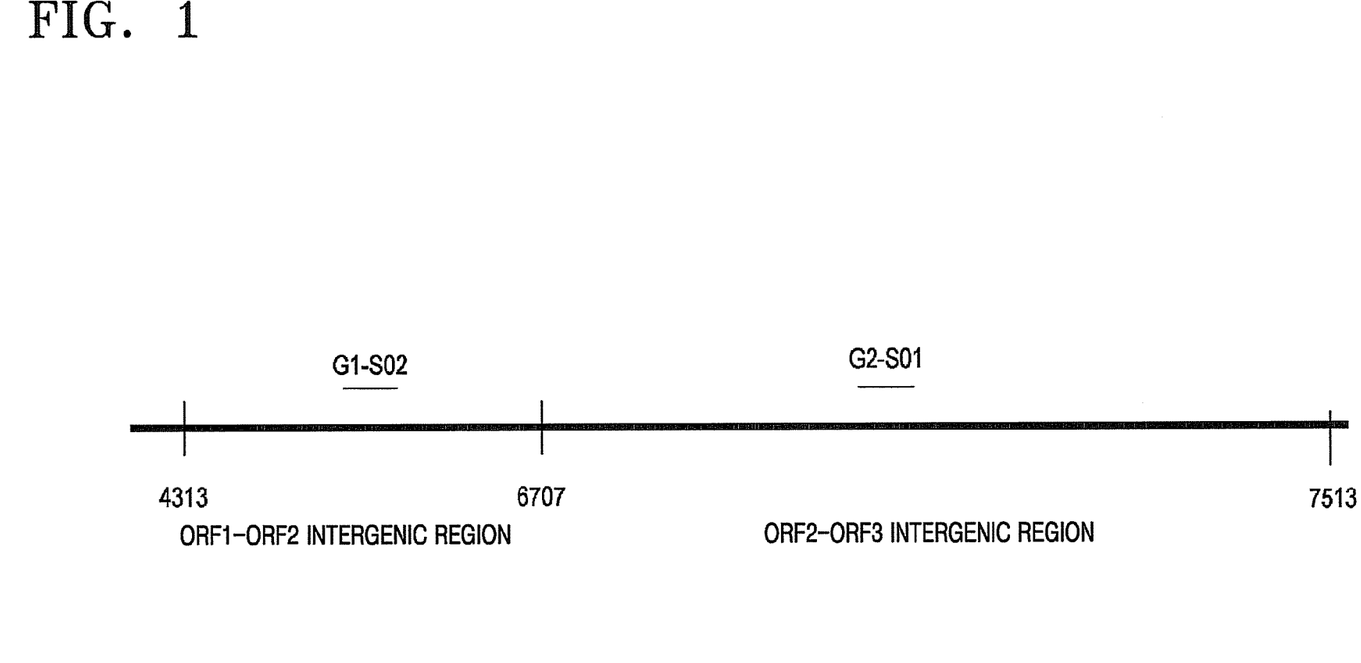
FIG. 1 is a diagram illustrating the positions of target sequences of the genomic RNA of norovirus.

When performing PCR using the primer set of the present invention, a target sequence region sought to be amplified is selected from a G1-SO2 region (ORF1-ORF2 intergenic region) and a G2-SO1 region (ORF2-ORF3 intergenic region) in norovirus. FIG. 1 is a diagram illustrating the positions of target sequences of the genomic RNA of norovirus (AY587989).

The primer set of the present invention was designed from the G1-SO2 region (the ORF1-ORF2 intergenic region) and the G2-SO1 region (the ORF2-ORF3 intergenic region) commonly found in 100 norovirus isolates. A primer set according to an exemplary embodiment of the present invention is presented in Table 1 below.

TABLE 1

Primer set according to an exemplary embodiment of the present invention

| Primer | SEQ ID NO: | Remark |
| --- | --- | --- |
| G1-SO2-F | 1 | Forward primer for G1-SO2 amplification |
| G1-SO2-R | 2 | Reverse primer for G1-SO2 amplification |
| G2-SO1-F | 3 | Forward primer for G2-SO1 amplification |
| G2-SO1-R | 4 | Reverse primer for G2-SO1 amplification |

SEQ ID NOS: 1 and 2, which constitute the primer set for G1-SO2 amplification, respectively have nucleotide sequences corresponding to positions 4763-4784 and 5086-5107 of AY587989 which is the genome sequence of a norovirus isolate, and SEQ ID NOS: 3 and 4, which constitute the primer set for G2-SO1 amplification, respectively have nucleotide sequences corresponding to positions 6891-6914 and 7047-7068 of AY587989. Thus, products amplified using these primer sets for G1-SO2 and G2-SO1 amplification are respectively 345 by and 178 by in length.

The present invention also provides an oligonucleotide probe or probe set capable of hybridizing with at least one target sequence of an intergenic region between ORF1 and ORF2 and an intergenic region between ORF2 and ORF3 in norovirus, the oligonucleotide probe or probe set being selected from the group consisting of:

an oligonucleotide probe capable of hybridizing with the intergenic region between ORF1 and ORF2 in norovirus, which includes at least one oligonucleotide selected from the group consisting of oligonucleotides including a fragment of at least 10 contiguous nucleotides present in at least one nucleotide sequence selected from the group consisting of nucleotide sequences as set forth in SEQ ID NOS: 5-8 and complementary oligonucleotides thereof; and an oligonucleotide probe capable of hybridizing with the intergenic region between ORF2 and ORF3 in norovirus, which includes at least one oligonucleotide selected from the group consisting of oligonucleotides including a fragment of at least 10 contiguous nucleotides present in at least one nucleotide sequence selected from the group consisting of nucleotide sequences as set forth in SEQ ID NOS: 9-11 and complementary oligonucleotides thereof.

The probe or probe set of the present invention may be an oligonucleotide probe or probe set capable of hybridizing with the intergenic region between ORF1 and ORF2 in norovirus, which includes at least one oligonucleotide selected from the group consisting of oligonucleotides including a fragment of at least 10 contiguous nucleotides present in at least one nucleotide sequence selected from the group consisting of the nucleotide sequences as set forth in SEQ ID NOS: 5-8 and complementary oligonucleotides thereof.

The probe or probe set of the present invention may be an oligonucleotide probe or probe set capable of hybridizing with the intergenic region between ORF2 and ORF3 in norovirus, which includes at least one oligonucleotide selected from the group consisting of oligonucleotides including a fragment of at least 10 contiguous nucleotides present in at least one nucleotide sequence selected from the group consisting of the nucleotide sequences as set forth in SEQ ID NOS: 9-11 and complementary oligonucleotides thereof.

The probe or probe set of the present invention may be an oligonucleotide probe set capable of hybridizing with the intergenic region between ORF1 and ORF2 and the intergenic region between ORF2 and ORF3 in norovirus, the oligonucleotide probe set including: an oligonucleotide probe capable of hybridizing with the intergenic region between ORF1 and ORF2 in norovirus, which includes an oligonucleotide including at least one nucleotide sequence selected from the group consisting of the nucleotide sequences as set forth in SEQ ID NOS: 5-8; and an oligonucleotide probe capable of hybridizing with the intergenic region between ORF2 and ORF3 in norovirus, which includes an oligonucleotide including at least one nucleotide sequence selected from the group consisting of the nucleotide sequences as set forth in SEQ ID NOS: 9-11.

The probe or probe set of the present invention specifically binds with PCR products amplified from target regions G1-SO2 and G2-SO1 commonly found in the genomic RNAs of noroviruses. Thus, the probe or probe set of the present invention can be used to detect norovirus. The probe or probe set of the present invention was designed by comparing sequences of the target regions G1-SO2 and G2-SO1 of the genomic RNAs of 100 norovirus isolates and selecting sequences commonly found in all the isolates.

As used herein, the term "probe" refers to a single-stranded nucleic acid sequence that can be hybridized with a complementary single-stranded target sequence to form a double-stranded molecule (hybrid).

In the specification, an oligonucleotide used as a primer or a probe may include a nucleotide analogue, e.g., phosphorothioate, alkylphosphorothioate, or a peptide nucleic acid, or an intercalating agent.

The present invention also provides a microarray in which a substrate is immobilized with at least one oligonucleotide probe or probe set according to an embodiment of the present invention.

As used herein, the term "microarray" refers to a high-density array of groups of polynucleotides immobilized on a substrate. Here, each group of the polynucleotides is a microarray immobilized in predetermined regions of the substrate. The microarray is well known in the art. Microarrays are disclosed in U.S. Pat. Nos. 5,445,934 and 5,744,305, the disclosures of which are incorporated herein in their entireties by reference. The oligonucleotide probe or probe set used in the microarray is as described above.

As used herein, the term "substrate" refers to a substrate which can be coupled with an oligonucleotide probe under conditions that retain hybridization characteristics and achieve low background hybridization. Conventionally, the substrate may be a microtiter plate, a membrane (e.g., nylon or nitrocellulose), a microsphere (bead), or a chip. A nucleic acid probe, before applied to or immobilized on a substrate, may be modified to facilitate probe immobilization or to enhance hybridization efficiency. The modification of the nucleic acid probe may include homopolymer tailing, coupling with a reactive functional group such as an aliphatic group, an $NH_2$ group, a SH group, or a carboxyl group, or coupling with biotin, hapten, or protein.

The present invention also provides a method of detecting norovirus, the method including:

contacting a sample with at least one oligonucleotide probe or probe set according to an embodiment of the present invention so that a target sequence of the sample hybridizes with a probe sequence; and detecting degree of hybridization between the probe sequence and the target sequence of the sample.

In the method of the present invention, the sample may include a PCR product obtained by RT-PCR using a primer set according to an embodiment of the present invention as primers and RNA derived from norovirus as a template.

As used herein, the term "RT-PCR" refers to reverse transcription-polymerase chain reaction. RT-PCR is a technique that is used to amplify cDNA (complementary DNA) reversely transcribed from a RNA template, and involves the following procedures: (1) synthesis of cDNA from RNA using reverse transcriptase; and (2) amplification of a specific site of cDNA. The procedure (2) is performed in the same manner as amplification of a specific gene site of genomic DNA.

Norovirus is RNA virus, and a 3'-end of the genomic RNA of norovirus has a poly(A) tail. Thus, in the present invention, cDNA is synthesized from RNA using one of an oligo d(T) primer and a primer according to an embodiment of the present invention and reverse transcriptase, and then, a target region of the cDNA is amplified using conventional PCR. As used herein, the "PCR" refers to a polymerase chain reaction and is a method for amplifying a target nucleic acid from a primer pair specifically binding with the target nucleic acid using a polymerase. PCR is well known in the art and can be performed using a commercially available kit. The amplification of a target nucleic acid can also be performed using an appropriate method known in the art, e.g., ligase chain reaction, nucleic acid sequence-based amplification, transcription-based amplification system, strand displacement amplification, Qβ replicase, or other nucleic acid amplification methods, in addition to PCR.

In the method of the present invention, the target sequence may be labeled with a detectable labeling material. For example, the labeling material may be a fluorescent material, a phosphorescent material, or a radioactive material, but the present invention is not limited thereto. Preferably, the labeling material may be Cy-5 or Cy-3. When the target sequence is amplified by PCR using primers, 5'-ends of which are labeled with Cy-5 or Cy-3, the target sequence can be labeled with the detectable labeling material. When performing PCR using a radioactive material, a radioisotope such as $^{32}P$ or $^{35}S$ is added to a PCR solution, and thus, a PCR product is labeled with the radioisotope incorporated into the PCR product.

In the method of the present invention, the oligonucleotide probe or probe set may be immobilized on a substrate of a microarray. The oligonucleotide probe or probe set immobilized on the microarray substrate is as described above.

In the method of the present invention, the hybridization may be performed under a high stringency hybridization condition. For example, the high stringency hybridization condition may be in a 0.12M phosphate buffer including equal moles of $Na_2HPO_4$ and $NaH_2PO_4$, 1 mM EDTA, and 0.02% sodium dodecylsulfate at 65° C. As used herein, the term "hybridization" refers to the bonding of two complementary strands of nucleic acid to form a double-stranded molecule (hybrid).

As used herein, "stringency" is the term used to describe a temperature and a solvent composition during hybridization and the subsequent processes. Under high stringency conditions, highly homologous nucleic acid hybrids will be formed. That is, hybrids with no sufficient degree of complementarity will not be formed. Accordingly, the stringency of assay conditions determines the amount of complementarity which should exist between two nucleic acid strands to form a hybrid. Stringency is chosen to maximize the difference in stability between probe-target hybrids and probe-non-target hybrids.

In the method of the present invention, the detection of norovirus can be achieved by labeling a PCR product with a detectable signal-emitting material, hybridizing the labeled PCR product with the oligonucleotide probe or probe set, and detecting a signal generated from the hybridization product. The detectable signal may be an optical signal or an electrical signal, but the present invention is not limited thereto. An optically active material may be a fluorescent material or a phosphorescent material. The fluorescent material may be fluorescein, Cy-5, or Cy-3. A PCR product may be unlabeled or labeled with a detectable signal-emitting material before or after hybridization. In a case where a PCR product is unlabeled, hybridization between the PCR product and a probe oligonucleotide can be detected by an electrical signal, but the present invention is not limited thereto.

Hereinafter, the present invention will be described more specifically with reference to the following examples. The following examples are for illustrative purposes only and are not intended to limit the scope of the invention.

EXAMPLES

Example 1

Figure 2:
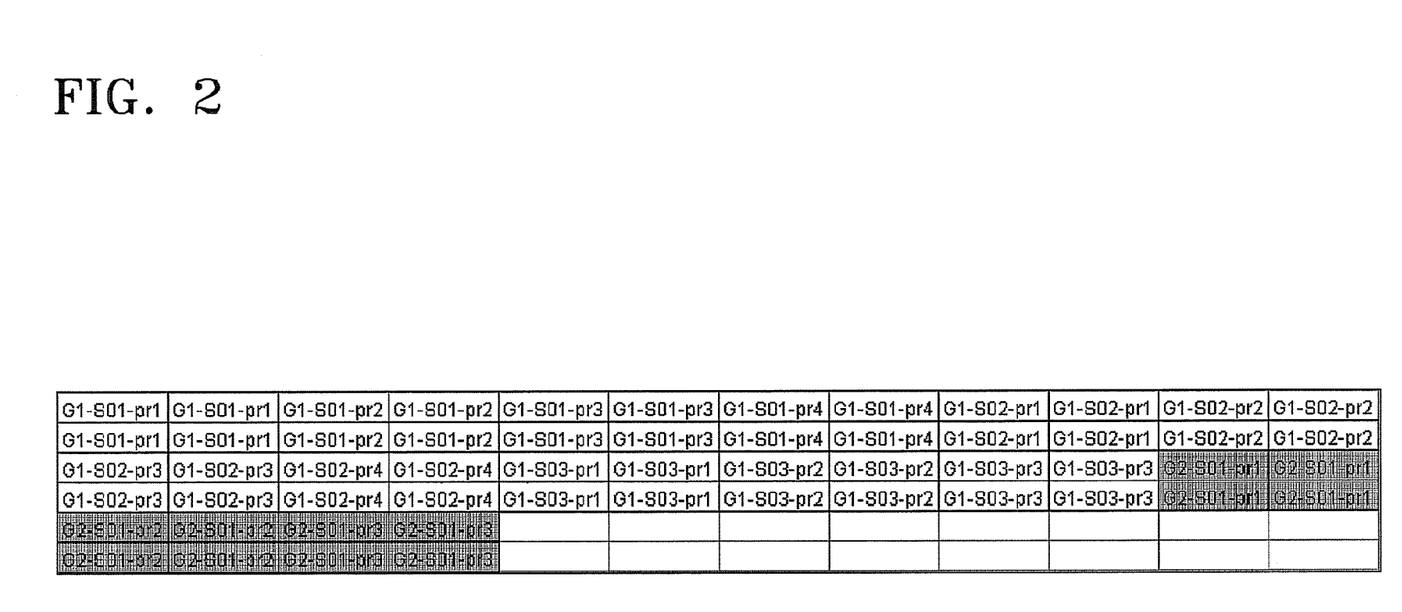
FIG. 2 is a view illustrating an array of spots of oligonucleotide probes immobilized on a microarray substrate.

Selection of Primers for Amplifying Target Sequences Commonly Found in Norovirus Isolates In Example 1, target sequences commonly found in genomic RNAs of 100 norovirus isolates were selected, and primer sets capable of amplifying the target sequences were designed.

First, the sequences of norovirus isolates were acquired from Genbank, and conserved regions of the genomic RNAs of the norovirus isolates were selected using DNASTAR program. 100 norovirus isolates were used in the experiments. As a result, two oligonucleotide primer sets were designed: an oligonucleotide primer set having sequences as set forth in SEQ ID NOS: 1 and 2 and an oligonucleotide primer set having sequences as set forth in SEQ ID NOS: 3 and 4. These oligonucleotide primer sets can respectively amplify the ORF1-ORF2 and ORF2-ORF3 intergenic regions in norovirus genomic RNAs.

Example 2

Amplification of Norovirus Genomic RNAs Using Primer Sets of the Present Invention The ORF1-ORF2 and ORF2-ORF3 intergenic regions of norovirus genomic RNAs were amplified using the two primer sets designed in Example 1.

First, RT-PCR was performed using the genomic RNAs of norovirus isolates (I) and (II) as templates and the two primer sets designed in Example 1 as primers to determine if each target sequence was specifically amplified.

(1) RNA Extraction

First, 560 μl of buffer AVL was put into a 1.5 ml tube. Then, 140 μl of a norovirus sample (for a solid sample, 10% (v/v) in PBS) was added to the tube and the reaction mixture was vortexed for 15 seconds. The reaction solution was incubated at room temperature (15~25° C.) for 10 minutes and centrifuged, and 560 μl of ethanol (96-100%) was added thereto. The resultant solution was thoroughly mixed while vortexing for 15 seconds and centrifuged. A 630 μl aliquot of the resultant solution was transferred to columns. The columns were centrifuged at 8,000 rpm for one minute, and collection tubes were twice replaced with new collection tubes. The columns were washed with 500 μl of a washing buffer and centrifuged at 8,000 rpm for one minute. 500 μl of buffer AW2 was added to the columns, the columns were centrifuged at 12,000 rpm for three minutes, and collection tubes containing an eluted solution were removed. The columns were transferred to a 1.5 ml new tube. 60 μl of an elution buffer was added to the columns. The columns were incubated for one minute and centrifuged at 8,000 rpm for one minute to elute RNAs.

(2) Reverse Transcription 2.5 μl of DMSO and 5 μl of the RNAs extracted from the sample were put into a PCR tube and thoroughly mixed. The mixture was centrifuged and incubated at 50° C. for three minutes. Immediately after the incubation, the RNA-containing solution was put into ice to induce RNA denaturation. At this time, the RNA-containing solution was maintained at a constant temperature using a PCR machine. 2 μl of a 10×RT buffer (FINZYME), 4 μl of dNTP (10 mM), 2.5 μl of a random hexamer ($N_6$) primer (10 pmole), 0.2 μl of M-MuLV reverse transcriptase (FINZYME), and 11.8 μl of distilled water treated with DEPC were thoroughly mixed to prepare 25 μl of a reverse transcription mixture, and the reverse transcription mixture was incubated at 60° C. for 15 minutes using TMC 1000 system to synthesize cDNAs.

(3) PCR

A PCR solution was prepared using 5.0 μl of the cDNAs prepared in (2) as templates, 5.0 μl of 5× Taq polymerase buffer, 0.3 μl of 10 mM dNTP mix, 4.0 μl of each primer (5 pmole), 1.0 μl of Taq polymerase, and 10 μl of sterilized water. The PCR solution was subjected to 25 cycles of denaturation at 95° C. for 15 seconds, annealing at 42° C. for 15 seconds, and extension at 68° C. for 15 seconds.

PCR products were analyzed by electrophoresis, demonstrating the presence of desired PCR products (data not shown).

Example 3

Detection of Noroviruses Using Microarrays

In Example 3, the PCR products obtained in Example 2 were allowed to hybridize with probes immobilized on microarrays, and the degree of probe-target hybridization was determined to detect the presence of a PCR product amplified from norovirus.

Sample preparation and PCR were performed in the same manner as in Example 2 except that 5'-ends of all forward and reverse primers were labeled with Cy-3. PCR products were detected using microarrays as follows.

Two norovirus isolates were used in the experiments. That is, norovirus samples (norovirus isolates (I) and (II)) were acquired from National Institute for Public Health.

(1) Probe Design

Probes were selected from amplified regions of norovirus genomes using DNASTAR program.

TABLE 2

| SEQ ID NO: | Probe | Target region |
|---|---|---|
| 5 | G1-SO2-pr1 | G1-SO2 |
| 6 | G1-SO2-pr2 | G1-SO2 |
| 7 | G1-SO2-pr3 | G1-SO2 |
| 8 | G1-SO2-pr4 | G1-SO2 |
| 9 | G2-SO1-pr1 | G2-SO1 |
| 10 | G2-SO1-pr2 | G2-SO1 |
| 11 | G2-SO1-pr3 | G2-SO1 |

(2) Manufacturing of Probe-Immobilized Microarrays

Wafers were spin-coated with a solution of GAPTES (γ-aminopropyltriethoxy silane) (20% (v/v)) or GAPDES (γ-aminopropyldiethoxysilane) (20% (v/v)) in ethanol. The spin coating was performed using a spin coater (Model CEE 70, CEE) as follows: initial coating at a rate of 500 rpm/10 sec and main coating at a rate of 2000 rpm/10 sec. After the spin coating was completed, the wafers were fixedly placed on a Teflon wafer carrier and cured at 120° C. for 40 minutes. The cured wafers were immersed in water for 10 minutes, ultrasonically washed for 15 minutes, immersed in water for 10 minutes, and dried. The drying was performed using a spin-drier. All the experiments were conducted in a clean room class 1000 where most dust particles had been sufficiently removed.

A probe set including probes having sequences as set forth in SEQ ID NOS: 5-11 was immobilized on the amino-activated wafers using a spotting method to thereby obtain microarrays.

(3) Detection

The PCR products were added on the microarrays. The microarrays were incubated at 42° C. for one hour so that probe-target hybridization occurred and then washed with a washing buffer. Fluorescence intensity was measured using a GenePix Scanner (Molecular Device, U.S.A.).

FIG. 2 is a view illustrating an array of spots of oligonucleotide probes immobilized on a microarray substrate. In FIG.

2, the probes of SEQ ID NOS: 5-8 were respectively spotted on regions represented by G1-SO2-pr1, G1-SO2-pr2, G1-SO2-pr3, and G1-SO2-pr4, the probes of SEQ ID NOS: 9-11 were respectively spotted on regions represented by G2-SO1-pr1, G2-SO1-pr2, and G2-SO1-pr3. Moreover, G1-SO1-pr1, G1-SO1-pr2, G1-SO1-pr3, G1-SO1-pr4, G1-SO3-pr1, G1-SO3-pr2, and G1-SO1-pr3, which are negative control probes having no sequence homology with G1-SO2 and G2-SO1 regions, were immobilized on respective corresponding regions.

Figure 3:
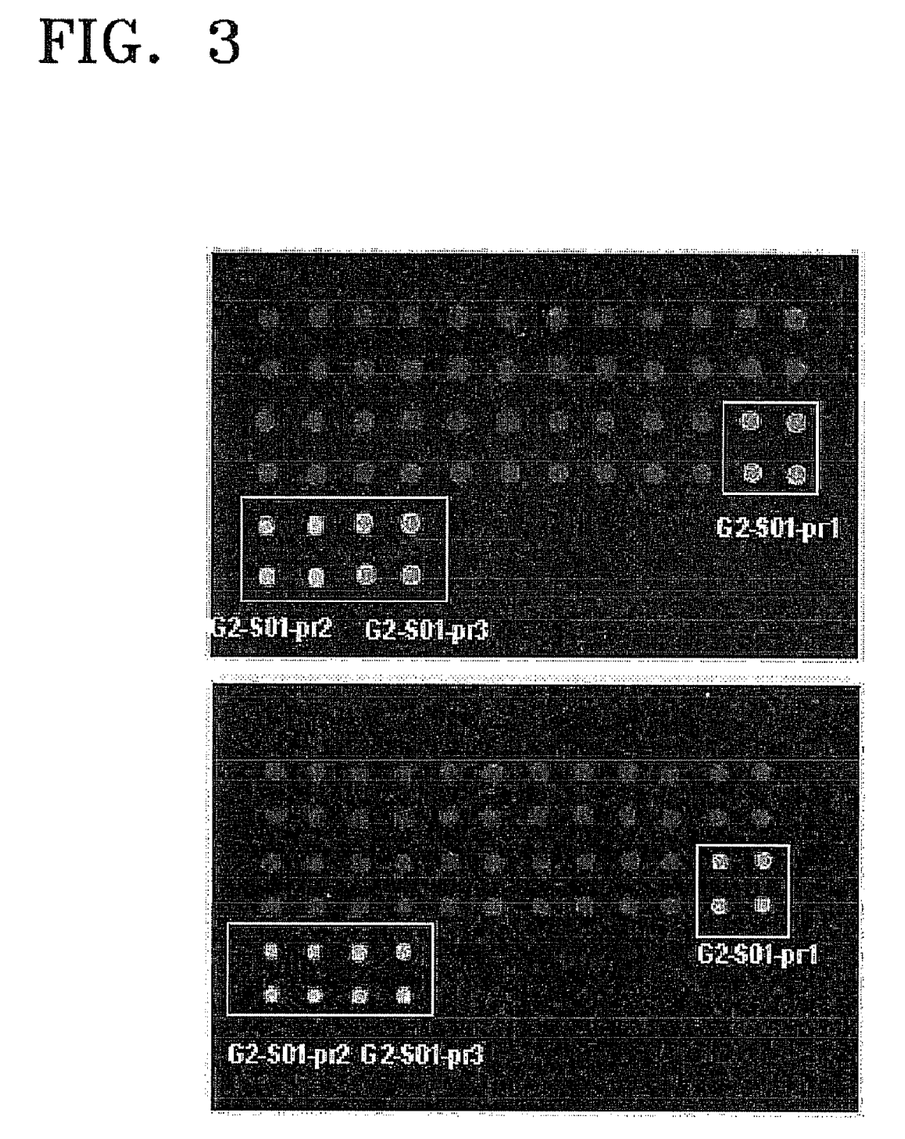
FIG. 3 is an image showing hybridization results of oligonucleotide probes immobilized on a microarray according to an embodiment of the present invention and PCR products obtained by PCR using a primer set as set forth in SEQ ID NOS: 3 and 4.

FIG. 3 is an image showing hybridization results of oligonucleotide probes immobilized on a microarray according to an embodiment of the present invention and PCR products obtained by PCR using a primer set as set forth in SEQ ID NOS: 3 and 4. In FIG. 3, an upper panel is hybridization results for the norovirus isolate (I), and a lower panel is hybridization results for the norovirus isolate (II). Referring to FIG. 3, positive hybridization signals are seen in microarray regions on which probes specific to the G2-SO1 region are immobilized, demonstrating that the primer set of SEQ ID NOS: 3 and 4 amplify the G2-SO1 region.

Therefore, norovirus can be detected with high sensitivity and 100% specificity using a probe of the present invention.

According to a primer set of the present invention, target sequences derived from various norovirus isolates can be amplified.

A probe or probe set of the present invention specifically hybridizes with a target sequence of a PCR product amplified using a primer set of the present invention, and thus, can be used for detection of various norovirus isolates.

A microarray of the present invention can be used for detection of various norovirus isolates.

According to a detection method of the present invention, various norovirus isolates can be efficiently detected with high specificity.

---

What is claimed is:

1. An oligonucleotide primer set for amplifying an intergenic region between ORF1 and ORF2 and an intergenic region between ORF2 and ORF3 in norovirus, which comprises an oligonucleotide set comprising the oligonucleotide consisting of the nucleotide sequence of SEQ ID NO: 1; and the oligonucleotide consisting of the nucleotide sequence of SEQ ID NO: 2; and an oligonucleotide set comprising the oligonucleotide consisting of the nucleotide sequence of SEQ ID NO: 3 and the oligonucleotide consisting of the nucleotide sequence of SEQ ID NO: 4.

* * * * *